(12) United States Patent
Smith

(10) Patent No.: US 6,835,819 B2
(45) Date of Patent: Dec. 28, 2004

US006835819B2

(54) SEQUENCES AND THEIR USE

(75) Inventor: Ulf Smith, Vallda (SE)

(73) Assignee: Metcon Medicin AB, Lidingo (SE)

( * ) Notice: Subject to any disclaimer, the term of this patent is extended or adjusted under 35 U.S.C. 154(b) by 17 days.

(21) Appl. No.: 09/875,945

(22) Filed: Jun. 8, 2001

(65) Prior Publication Data

US 2002/0098169 A1 Jul. 25, 2002

Related U.S. Application Data

(60) Provisional application No. 60/210,207, filed on Jun. 8, 2000.

(30) Foreign Application Priority Data

Jun. 9, 2000 (SE) .............................. 0002189

(51) Int. Cl.[7] ........................ C07H 19/00; C07H 21/02; C12P 21/06
(52) U.S. Cl. ...................... 536/22.1; 536/23.1; 435/69.1
(58) Field of Search .............................. 536/22.1, 23.1; 435/69.1

(56) References Cited

U.S. PATENT DOCUMENTS 5,478,852 A   12/1995   Olefsky et al. ............. 514/369
5,578,444 A   11/1996   Edwards et al.
5,858,701 A    1/1999   White et al. ................ 435/69.1

FOREIGN PATENT DOCUMENTS

WO          98/21592         5/1998
WO          98/56909        12/1998

OTHER PUBLICATIONS

Birren et al. *Homo sapiens*, clone RP11–16C4. submitted to Whitehead Institute/ MIT Center for Genome Research, Oct. 15, 1999.*

* cited by examiner

*Primary Examiner*—Jeffrey Fredman
*Assistant Examiner*—Suryaprabha Chunduru
(74) *Attorney, Agent, or Firm*—Young & Thompson

(57) ABSTRACT

Novel non-coding sequences isolated upstream of the human IRS-2 gene are disclosed as markers for the prediction and/or diagnosis of IRS-2 related metabolic disorders or diseases, such as diabetes. The sequences also fuction as markers in a method and assay for evaluating the insulin regulating, i.e. insulin sensitizing or inhibiting properties of drug candidate substances, e.g. a method and assay for high throughput screening. The sequences and/or information derived therefrom can also be used for influencing the expression of the IRS-2 gene, e.g. in the therapy of IRS-2 related metabolic disorders, such as diabetes.

7 Claims, 8 Drawing Sheets

IRS-2 ip

Figure 1A:
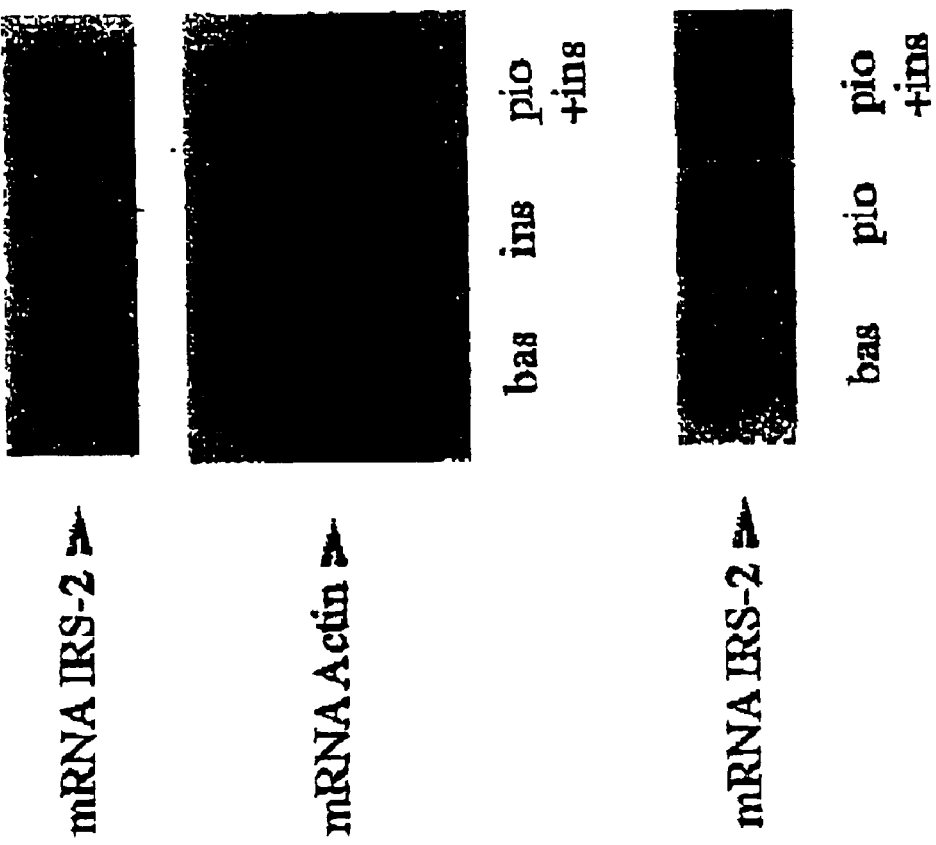

Fig. 2 mRNA IRS-2 ins    dar
       +ins ins    WY    pio    WY
                    +ins bas    prog   prog   8-Br   8-Br
              +pio          +pio

IRS-1 ip

PS- PKB ➤

PThr- PKB ➤ bas   ins   pio   pio +ins ins   +   +   +   +

| | | | | | | |
|---|---|---|---|---|---|---|
| (7) rev1487 | GGTAGGTGATTCTTACCTT | GATAAG | T | AGGTCA | C | CATCTA TCCAGTTGTGCAGCTGGAAACCTG |
| (5) 3398 | ATGCTTTGCTCTTCT | CTATTC | T | AGGTCA | T | TCATTC CATCACAACCTCTGGAATTTCCACAT |
| (6) 4474 | TCCTCTC | AGATGC | C | AGGTCA | C | ACTTCC AGGCTACAGCTGAACTT |
| (4) 4606 | AGGTGGA | TTGCTT | G | AGGTCA | G | GAGTTT GAGACCAACTCAGCCAACATGGT |
| (3) 5956 | CTCCTCGCATTGCCAT | ATTTGT | G | AGGTCA | C | TTGCAG TAGGTATCTGTGTGCACA |
| (2) 6553 | CATTATTGTGAAATT | TGTATT | C | AGGTCA | T | TCACCA ATTTTTAGAAATGTTTT |
| (8) rev7001 | GAACCTACACATGAACATAGCCA | AATCAA | A | AGGTCA | G | TTGTAT TTGGTACAGAACT |
| (1) 9558 | AAAAGAATGTGA | GACTTA | A | AGGTCA | A | TGTAGG GGAGAAATACAATTAAAAA |
| (9) +18934 | GCCCCCGGACCCCCACCGC | GGCGCC | A | AGGTCA | T | CCGCGC AGACCCGCAGGGGGCCGCCGCC |
| (10) +19719 | GGGGCACAA | CAAGGC | A | AGGTCA | C | CTGCCT CTTTCCCTTGTTCCCGG |
| (11) +21283 | ATAATGTT | AGCTGG | A | AGGTCA | A | TTTCAG TGTATGATATACTTTATTAAGATGTATA |
| (12) +22657 | GAGGCAGGCAGA | TCACCT | G | AGGTCA | G | GAGTTC GAGACAAGCCTGACCAACATGGAGAAA |

Fig. 5

SEQUENCE LISTING

<160> NUMBER OF SEQ ID NOS: 14

<210> SEQ ID NO 1
<211> LENGTH: 53
<212> TYPE: DNA
<213> ORGANISM: Homo sapiens

<400> SEQUENCE: 1
aaaaagaatg tgagacttaa aggtcaatgt aggggagaaa tacaattaaa aaa         53

<210> SEQ ID NO 2
<211> LENGTH: 51
<212> TYPE: DNA
<213> ORGANISM: Homo sapiens

<400> SEQUENCE: 2
cattattgtg aaatttgtat tcaggtcatt caccaatttt tagaatgttt t           51

<210> SEQ ID NO 3
<211> LENGTH: 52
<212> TYPE: DNA
<213> ORGANISM: Homo sapiens

<400> SEQUENCE: 3
ctcctcgcat tgccatattt gtgaggtcac ttgcagtagg tatctgtgca ca          52

<210> SEQ ID NO 4
<211> LENGTH: 50
<212> TYPE: DNA
<213> ORGANISM: Homo sapiens

<400> SEQUENCE: 4
aggtggattg cttgaggtca ggagtttgag accaactcag ccaacatggt             50

<210> SEQ ID NO 5
<211> LENGTH: 61
<212> TYPE: DNA
<213> ORGANISM: Homo sapiens

<400> SEQUENCE: 5

```
atgctttgct cttctctatt ctaggtcatt cattccatca caacctctgg aatttccaca      60
t                                                                      61
```

<210> SEQ ID NO 6
<211> LENGTH: 44
<212> TYPE: DNA
<213> ORGANISM: Homo sapiens

<400> SEQUENCE: 6

```
tcctctcaga tgccaggtca cacttccagg ctacagctga actt                       44
```

<210> SEQ ID NO 7
<211> LENGTH: 63
<212> TYPE: DNA
<213> ORGANISM: Homo sapiens

<400> SEQUENCE: 7

```
ggtaggtgat tcttaccttg ataagtaggt caccatctat ccagttgtgc agctggaaac      60
ctg                                                                    63
```

<210> SEQ ID NO 8
<211> LENGTH: 54
<212> TYPE: DNA
<213> ORGANISM: Homo sapiens

<400> SEQUENCE: 8

```
gaacctacat gaacatagcc aaatcaaaag gtcagttgta tttggtacag aact            54
```

<210> SEQ ID NO 9
<211> LENGTH: 62
<212> TYPE: DNA
<213> ORGANISM: Homo sapiens

<400> SEQUENCE: 9

```
gcccccggac ccccaccgcg gcgccaaggt catccgcgca gacccgcagg ggggccgccg      60
cc                                                                     62
```

<210> SEQ ID NO 10
<211> LENGTH: 46
<212> TYPE: DNA
<213> ORGANISM: Homo sapiens

<400> SEQUENCE: 10

```
ggggcacaac aaggcaaggt cacctgcctc tttcccttgt tcccgg                     46
```

<210> SEQ ID NO 11
<211> LENGTH: 56
<212> TYPE: DNA
<213> ORGANISM: Homo sapiens

<400> SEQUENCE: 11

```
ataatgttag ctggaaggtc aatttcagtg tatgatatac tttattaaga tgtata         56
```

<210> SEQ ID NO 12
<211> LENGTH: 59
<212> TYPE: DNA
<213> ORGANISM: Homo sapiens

<400> SEQUENCE: 12

-continued

```
gaggcaggca gatcacctga ggtcaggagt tcgagacaag cctgaccaac atggagaaa      59
```

<210> SEQ ID NO 13
<211> LENGTH: 21
<212> TYPE: DNA
<213> ORGANISM:

<400> SEQUENCE: 13

```
cgagaggccg cgacccaaca c                                               21
```

<210> SEQ ID NO 14
<211> LENGTH: 23
<212> TYPE: DNA
<213> ORGANISM:

<400> SEQUENCE: 14

```
aggcggccgc acatcatctc gta                                             23
```

SEQUENCES AND THEIR USE

This application claims the benefit of Provisional Application No. 60/210,207 filed on Jun. 8, 2000.

The present invention relates to metabolic disorders or diseases, their prediction, diagnosis, prevention, and treatment. The invention in particular relates to IRS-2 related metabolic disorders or diseases, such diabetes and obesitas, and makes available specific nucleotide sequences and their therapeutic and diagnostic use, as well as their use as research tools, inter alia a novel method and assay for screening drug candidates and for differentiating between and evaluating insulin regulating substances.

BACKGROUND OF THE INVENTION

Metabolic disorders or diseases are conditions, where the distribution of nutrients and their use, including the elimination of wastes, in a living body is disturbed or disrupted. IRS-2 related metabolic disorders or diseases are abnormal conditions, where the activation, expression or other function of the IRS-2 gene is involved.

Diabetes mellitus is a complex disorder of carbohydrate, fat, and protein metabolism that is primarily a result of a relative or complete lack of insulin secretion by the beta cells of the pancreas or a result of defects of the insulin receptors. The various forms of diabetes are divided in two categories, the most frequent being juvenile-onset diabetes or Type I insulin-dependent diabetes mellitus (IDDM) and adult-onset diabetes or Type II non-insulin-dependent diabetes mellitus (NIDDM), Both diseases, even when correctly diagnosed and medicated, require life-long medication, good patient compliance, a careful diet and frequent medical observation to avoid potentially serious sequelae.

Thiazolidinediones (TZD) are a recently identified class of antidiabetic agents which act by improving insulin sensitivity in both different animal models of obesity and diabetes as well as in man. In addition to improving the glucose and insulin levels, the circulating free fatty acids (FFA) and triglycerides are also lowered.

TZD promote fat cell differentiation and activate several adipocyte-specific genes such as the fatty acid binding protein, aP2, as well as the lipoprotein lipase. There is much recent evidence that TZD induce their diverse effects by binding to and activating the peroxisome proliferator activated receptor (PPAR)γ (reviewed in Spiegelman, 1998). PPARγ is mainly expressed in the adipose tissue and exists as two isoforms, PPARγ1 and γ2. PPARγ1 is the major isoform and accounts for around 85% of that in the adipose tissue. The isoforms differ in their $NH_2$-terminal end, with PPARγ2 having additional 30 amino acids, and are generated from the same gene by mRNA splicing.

It is currently unclear how TZD improve insulin sensitivity since known PPARγ-regulated genes mainly involve adipocyte differentiation, lipid storage and metabolism. It is also noted, however not yet explained, that a number of patients fail to respond to TZD treatment. The percentage vanes between different demographic groups, but may on average amount to as much as 30% of all patients. Due to the complex nature of the disease, the fact that a certain patient fails to respond to the treatment will not become evident until after several weeks of treatment and re-admission or a repeated visit to the physician.

Current hypotheses of the mechanisms for the direct insulin regulating or sensitizing effect of TZD include; the formation of new, small and insulin-sensitive fat cells; the inhibition of TNFα production and, hence, its negative effects on insulin signaling or, as found in some experiments, increased GLUT4 expression in adipocytes although this requires activation of C/EBPα, as well. However, no clear and reproducible link to the intracellular signaling molecules for insulin has been found so far.

PRIOR ART

In U.S. Pat. No. 5,478,852, Olefsky et al. disclose methods of using thiazolinedione derivatives and related antihypoglycemic agents in the treatment of impaired glucose tolerance in order to prevent or delay the onset of noninsulin-dependent diabetes mellitus. This reference is however silent on the underlying mechanism of action, responsible for the treatment effects disclosed therein.

In WO 98/21592, Smith and Rondinone disclose methods for screening candidate bioactive agents capable of modulating the activity of IRS-1 and IRS-2, collectively called IRS-molecules. The methods are characterised in that a candidate bioactive agent is added to a sample of the IRS-molecule, whereafter the binding of said candidate agent to said IRS-molecule is determined. Alternatively, the activity of the IRS-molecules is measured before and after the addition of the candidate agent. Neither coding nor non-coding sequences related to IRS-2 are disclosed.

In U.S. Pat. No. 5,858,701, White et al. disclose a nucleic acid sequence encoding an IRS-2 polypeptide, claiming to have discovered the existence of a family of IRS-2 like genes, which share functional and structural properties. These coding sequences, which notably may exhibit variations between population groups and even individuals, are suggested for use in gene therapy, diagnosis of disease, determination of the risk of developing a disease, evaluation of an effect of a treatment, and evaluation of a compound for the ability to bind a nucleic acid encoding an IRS regulatory sequence.

Obviously, the IRS-protein itself and its corresponding coding sequence has been studied and used as the marker, either directly by measuring its activity or concentration, or indirectly, by studying its interaction with other molecules. The non-coding sequences have however, to the best knowledge of the present inventor, hitherto not been identified as such neither suggested for use for research, screening, diagnostic nor therapeutic purposes.

There remains a need to improve the treatment of metabolic, IRS-2 related disorders, such as diabetes and in particular to develop new pharmaceuticals for this purpose, e.g. improved methods for differentiating between insulin regulating, i.e. insulin sensitizing or inhibiting substances. In particular, new, specific, and reliable markers for IRS-2 transcription are needed. One problem to be solved is therefor how to efficiently, and accurately screen candidate drugs, e.g. the class of TZD compounds in respect of insulin regulating, i.e. insulin sensitizing or inhibiting properties in different cells. Another problem is to find genetic markers with wide applicability, useful for the diagnosis of diseases related to abnormal IRS-2 transcription and for the determination of the risk of developing such diseases.

Further problems and their solutions will become evident or possible to deduce from the following description, example and claims.

SUMMARY OF THE INVENTION

The above problems and shortcomings of the prior art are solved by invention as set forth in the attached sequence listing and claims, which are hereby incorporated in their entirety. The present inventor has identified specific non-coding sequences upstream to the known IRS-2 gene. These are disclosed in the attached sequence listing (PatentIn 2.1) and numbered SEQ.ID.NO. 1–12. By using at least one of these sequences or closely homologous sequences as the reporter(s) for the evaluation of IRS-2 activation, a more practical and generally applicable assay system is made possible. Similarly, by using at least one of these sequences or closely homologous sequences as the reporter(s) for the evaluation of IRS-2 activation, a more accurate prediction and diagnosis is made possible. Further advantages, embodiments and characteristics of the invention will be evident from the following description and examples.

SHORT DESCRIPTION OF THE FIGURES

The present invention will be disclosed in detail below, in the description and attached examples and figures, in which FIG. 1(A) top—shows the IRS-2 mRNA expression (Northern blots) in differentiated 3T3-L1 adipocytes cultured for 48 hrs with no additions (bas), 100 nM insulin (ins) or 10 $\mu$M pioglitazone (pio) in combination with 100 nM insulin. Actin mRNA is also shown for the same cells. bottom—shows IRS-2 mRNA levels from cells cultured for 48 hrs with no additions (bas), with 10 $\mu$M pioglitazone (pio) with or without 100 nM insulin (pio+ins). (B) top—shows individual data from 5 experiments where IRS-2 mRNA was related to β-actin gene expression in the same cells (arbitrary units). Bars represent mean values. bottom—IRS-2 protein expression in differentiated 3T3-L1 cells cultured for 48 hrs with no additions (bas), with 100 nM insulin (ins) or with 10 $\mu$M pioglitazone (pio). The scanned data are also shown below (arbitrary units). (C) Time-course for IRS-2 mRNA expression in differentiated 3T3-L1 adipocytes cultured with 10 $\mu$M pioglitazone for the indicated times. The values represent % increase over non-stimulated control cells and are the means of two experiments.

FIG. 2 top—shows IRS-2 mRNA in differentiated 3T3-L1 adipocytes cultured for 48 hrs with 100 nM insulin (ins) alone or with 10 $\mu$M darglitazone (dar). middle—shows IRS-2 mRNA in cells cultured with 100 $\mu$M insulin (ins), 10 $\mu$M of the PPARα agonist WY14643 (WY), with or without 100 nM insulin, and 10 $\mu$M pioglitazone (pio). bottom—shows IRS-2mRNA from differentiated cells that had been cultured for 48 hrs with no additions (bas), 100 nM progesterone (prog) with or without 10 $\mu$M pioglitazone (pio) or 200 $\mu$M 8-BrcAMP with or without pioglitazone.

Figure 3A:
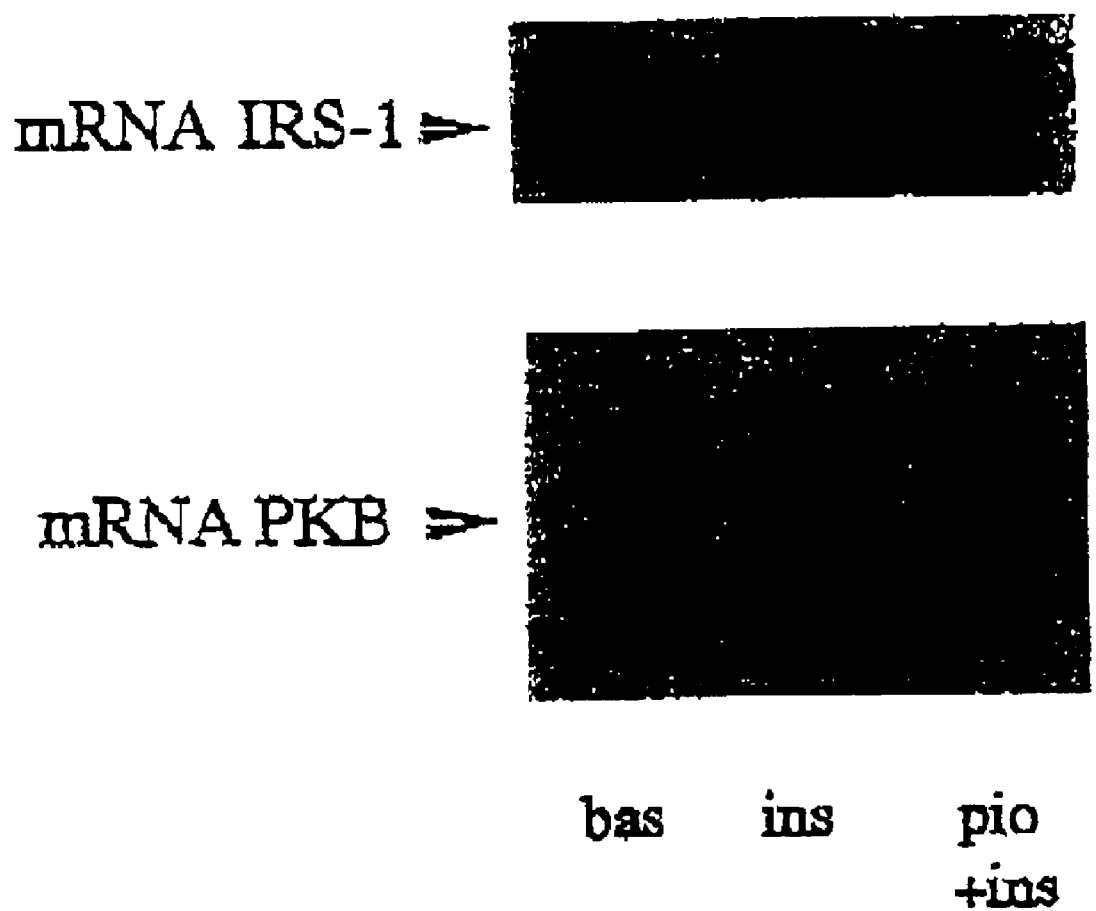

FIG. 3(A) shows IRS-1 and PKB/Akt mRNA in differentiated 3T3-L1I adipocytes cultured for 48 hrs with no additions (bas), 100 nM insulin (ins) or 10 $\mu$M pioglitazone (pio) with insulin. (B)top—Individual data from 5 experiments (same as shown in FIG. 1B) where IRS-1 mRNA was related to β-actin gene expression in the same cells (arbitrary units). Bars represent mean values. bottom—IRS-1 protein expression in differentiated 3T3-L1 cells cultured for 48 hrs with no addition (bas), 100 nM insulin, 10 $\mu$M pioglitazone (pio) with or without 100 nM insulin. The scanned data are also shown below (arbitrary units).

Figure 4:
Figure 4:

FIG. 4 shows an immunoblot of serine- or threonine-phosphorylated PKB. Lysates were prepared from cells that had been cultured for 48 hrs as in FIG. 3A, serum-starved for 3 hrs, and then stimulated with 100 nM insulin for 10 min. Following separation on 7.5% SDS-PAGE, the proteins were immunoblotted with antibodies recognizing insulin-stimulated phosphoserine (PS-PKB) and phosphothreonine (PThr-PKB) PKB/Akt.

FIG. 5 shows an alignment chart of the inventive sequences, SEQ. ID. NO.1 trough 12, based on an alignment of the PPAR binding site, AGGTCA, contained in each sequence.

DESCRIPTION

In the present description, the term "metabolic disorder" is intended to encompass any pathophysiologic dysfunction that results in a loss of metabolic control of homeostasis in the human or animal body. Examples of such disorders or diseases include, but are not limited to, e.g. diabetes and obesitas.

The term "metabolic IRS-2 related disorder" encompass any disorder involving the insulin receptor substrate molecule IRS-2, the protein and its corresponding nucleotide sequences, their activation, expression or inhibition.

The term "insulin regulating substance" encompasses any substance capable of interfering or interacting with insulin in its role in the regulation of the metabolism of glucose, fats, carbohydrates, and proteins. The term "regulating" encompasses both sensitization and inhibition of insulin, the potentiation and the blocking of the effects of insulin in the human or animal body.

The terms "treatment", "therapy", "therapeutic use", "medicament", and "medical use" encompass both human and animal or veterinary applications.

The present inventor has examined in differentiated 3T3-L1 adipocytes the effect of PFARα and γ ligands on the expression of several key molecules for insulin signaling and action; IRS-1, IRS-2, PKB/Akt and GLUT4. It was surprisingly and unexpectedly found, that the only gene, which was rapidly and reproducibly increased was IRS-2, and his was also associated with an increased protein expression. Pioglitazone was found to induce tanscription of the IRS-2 gene, resulting in a major transcript having a molecular weight of 7.2 kb. A minor transcript having a molecular weight of 8.2 kb was also frequently detected.

In the present study, the present inventor demonstrates for the first time that PPARγ activation, but not PPARα, rapidly turns on the gene of the key signaling molecule IRS-2. This effect was initiated after 4 hrs, peaked after 24 hrs and remained elevated throughout the 48 hrs study. Furthermore, this effect appeared specific since, under the same conditions and in the same cells, no effects on IRS-1, PKB/Akt or GLUT4 were seen. Thus, it was not related to a general effect on cell differentiation by the PPARγ ligands. In addition, IRS-2 protein expression was also increased (~40%) after 48 hrs and its signaling through the PI3-kinase and PKB/Akt pathway also tended to be increased. Since the IRS-2 gene activation was rapid and seen in the presence of the protein synthesis inhibitor, cycloheximide, the data suggest a direct effect of PPARγ activation on the IRS-2 promoter. However, this has to be directly tested in appropriate reporter assays.

The partial human IRS-2 gene and promoter were recently cloned and sequenced (Vassen et al, 1999) but the complete murine promoter has not been reported. Interestingly, progesterone and cAMP were found to increase the expression of the IRS-2 gene in HeLa cells but GRE/PRE were not identified in the promoter. Sequencing the promoter identified multiple binding sites for several transcription factors such as Sp1, AP2 and CCAAT-box binding factor. However, the identified sequence in the human IRS-2 promoter (Mangelsdorf and Evans, 1995) does not contain the typical AGGTCA binding sites for PPAR. Studies with appropriate reporter systems are necessary to clarify if PPARγ ligands directly activate the mouse and/or human IRS-2 genes. Interestingly, preliminary studies by the present inventor have shown that pioglitazone also increases IRS-2 gene expression in human fat cells from type 2 diabetic individuals.

Insulin alone did not change the IRS-2 gene expression and there was no synergistic effect between TZD and insulin. These latter data must be interpreted with some caution since the serum in the culture medium contains insulin. Surprisingly, no effect of either progesterone or cAMP on IRS-2 gene expression in 3T3-L1 cells could be seen. This is in contrast to recent data in HeLa cells where these agents increased IRS-2 mRNA levels but this may be an indirect effect and not seen in all cells.

Similar to IRS-2, chronic exposure to insulin did not change IRS-1 gene expression. However, in contrast to IRS-2, IRS-1 protein expression was reduced after chronic insulin stimulation in the 3T3-L1 cells as also reported by others. This effect of chronic marked hyperinsulinemia is then probably due to an increased protein degradation. Recent studies have shown that chronic exposure to insulin leads to an increased serine/threonine phosphorylation through the PI3-kinase and PKB/Akt pathway. IRS-1 is then degraded through the proteasomal pathway probably as a result of ubiquination.

Cells chronically exposed to the high insulin concentration also had an impaired acute response to insulin, which probably was due to an impaired activation of PI3-kinase and the down-stream signaling. This was seen by the reduced phosphorylation of PKB on both serine and threonine sites. The addition of pioglitazone did not clearly improve the insulin effect. These data are in agreement with the concept that IRS-1 is the major docking protein for PI3-kinase in response to insulin in both 3T3-L1 cells (Sun et al., 1997) as well as in human fat cells and that IRS-2 functions as a true "back-up" protein.

However, it is still surprising that the increased IRS-2 protein expression was unable to clearly improve the PI3-kinase activity and downstream signaling. These results are similar to recent findings in IRS-1 "knock-out" cells as well previous findings by the present inventor in human fat cells from Type 2 diabetic subjects, where IRS-2 expression is nodal but IRS-1 protein expression is reduced ~70% (Rondinone et al., 1997). PKB activation and phosphorylation remained impaired in these cells even in the presence of supramaximal insulin concentrations. Whether longer exposure to TZD than the 48 hrs used in this study will further increase IRS-2 protein expression and restitute the insulin response remains to be established.

Furthermore, it will be of interest to see if the low IRS-1 expression in fat cells from Type 2 diabetic subjects as well as in the cohort the present inventor have identified of non-diabetic but markedly insulin-resistant individuals with a genetic predisposition for diabetes will be compensated for by an increased IRS-2 expression following TZD.

In summary, the present data show for the first time a clear link between PPARγ ligands and the insulin signaling cascade in that TZD rapidly increase IRS-2 gene (and protein) expression in 3T3-L1 cells. Since IRS-2 appears to play a profound role in diabetes, these data suggest that the antidiabetic effect of TZD may be mediated through this effect. It will also be of great interest to see if TZD can influence β-cell growth and/or apoptosis since a stunning effect of IRS-2 gene disruption is seen on pancreatic β-cell development. Thus, although IRS-2 can also be used by insulin as a docking protein for PI3-kinase activation, it may play an even more profound role in the signaling and effect of cytokines and growth factors.

The expression of several genes involved in insulin signaling and action were examined after 4–48 hrs exposure to different concentrations of pioglitazone (pio). However, only the IRS-2 gene expression was consistently increased. The IRS-2 mRNA included a major ~7.2 Kb band but a minor band at ~8.2 Kb was also frequently seen.

Within the priority year, the 10 kb genomic sequence immediately upstream of the open reading frame of the human IRS-2 gene was sequenced, resulting in the sequences SEQ. ID. NO. 1 through 12, disclosed in the attached sequence listing (PatentIn 2.1).

As there always are single individuals or groups, within any population, exhibiting minor genetic variations, such as single base deletions, substitutions or mutations, the disclosed sequences are understood to encompass closely homologous sequences, that is sequences exhibiting 70, 80, 90, 95, or 98% homology to any one of the sequences disclosed as SEQ. ID. NO. 1 through 12. The invention also encompasses sequences capable of hybridising under stringent conditions to any one of the sequences disclosed as SEQ. ID. NO. 1 through 12. The invention also encompasses the complementary sequences corresponding to SEQ. ID. NO. 1 through 12.

It is of great importance to be able to predict the risk of developing metabolic disorders or diseases, to prevent or delay the onset of such disorders or diseases, to diagnose and to treat such disorders or diseases, in particular IRS-2 related disorders or diseases, e.g. diabetes or obesitas. As the present inventor has isolated and sequenced specific non-coding sequences immediately upstream of the human IRS-2 gene, which can be used as markers for the diagnosis or prediction of IRS-2 related disorders or diseases, or for the prevention and/or treatment thereof.

It is of commercial value to be able to control the IRS-2 level to thereby regulate insulin sensitivity in adipocytes and other cells to normalize metabolism in insulin-related disorders, for example type II diabetics or obesitas. The findings disclosed above constitute a basis for finding such regulating substances, not only for human or mammalian adipocytes but also for other, specific human or mammalian cells such as hepatic cells, pancreatic cells or muscle tissue cells. The findings also constitute a basis for finding insulin regulating compounds, i.e. sensitizing or inhibiting compounds for veterinary use, e.g. for the treatment of animals kept for economical or emotional reasons, such as livestock, cattle, horses and pets. The treatment of animals in this context includes both the treatment in the sense of improving health or preventing disease, and also any treatment aiming at changing growth parameters, such as meat production.

According to one embodiment of the invention, at least one of SEQ. ID. NO. 1 through 12, or homologues thereof is used as a marker or as markers to screen and find compounds possessing insulin regulating, i.e. sensitizing or inhibiting properties in different cells. The detection of the sequence(s) may be done directly, e.g. using PCR, or indirectly, using a suitable reporter system. Preferably, the detection is facilitated by coupling said at least one of SEQ. ID. NO.1 through 12, or a homologue thereof, to a suitable reporter, e.g. a fluorescent reporter molecule.

According to one embodiment of the invention, at least one of SEQ. ID. NO. 1 through 12, or homologues thereof, is used as a marker or as markers to screen the class of TZD compounds in respect of insulin regulating, i.e. insulin sensitizing or inhibiting properties in different cells. The detection of the sequence(s) may be done directly, e.g. using PCR, or indirectly, using a suitable reporter system. Preferably, the detection is facilitated by coupling said at least one of SEQ. ID. NO. 1 through 12, or a homologue thereof, to a suitable reporter, e.g. a fluorescent reporter molecule.

According to yet another embodiment, at least one of the above SEQ. ID. NO.1 through 12 is used as a specific marker to screen and find adipocyte specific insulin regulating substances, i.e. insulin sensitizers or inhibitors using appropriate mammalian cells and subsequent detection of the at least one sequence. The detection of the sequence(s) may be done directly, e.g. using PCR, or indirectly, using a suitable reporter system. Preferably, the detection is facilitated by coupling said at least one of SEQ. ID. NO. 1 through 12, or a homologue thereof, to a suitable reporter, e.g. a fluorescent reporter molecule. Suitable screening systems include, but are not limited to Northern blots, RT-PCR using specific primers and probes for IRS-2, solution hybridisation and RNA'ase protection assays.

Large scale screening, e.g. so called high throughput screening (HTS) of chemical libraries can be performed with a reporter system, adapted for specific sequences of the IRS-2 promotor, in particular a sequence chosen among SEQ. ID. NO. 1–12, or homologues thereof. Useful reporter sequences are luciferase or similar, sensitive assays.

According to a further embodiment of the invention, this at least one marker as disclosed above is used in a screening system to find and discriminate between insulin regulating substances, i.e. insulin sensitizers or inhibitors acting on different cells, such as blood cells, hepatic cells, muscle tissue cells and adipocytes.

The detection of the above at least one sequence chosen from SEQ. ID. NO. 1 through 12 is performed either qualitatively or quantitatively. Qualitative detection methods comprise any method where the presence or absence of a marker is determined, e.g. based on radiation, fluorescence, etc. Quantitative methods comprise any method where the amount of marker is determined, e.g. qualitative PCR or RT-PCR.

Preferably, the at least one sequence chosen from SEQ. ID. NO. 1 through 12 or information derived therefrom is/are used for the production of an assay for the screening of drug candidates in respect of their insulin regulating properties. Most preferably, said assay is constructed as an assay suitable for high throughput (HTP) screening, for example an assay adapted for the commonly used 96-well format, the 384-well format or denser formats, such as micro arrays or chips, carrying immobilised reagents on their surface.

The invention also encompasses novel compounds exhibiting therapeutic properties, e.g. insulin regulating, e.g. insulin sensitizing or inhibiting properties, identified using the methods disclosed above. The invention also encompasses the medical use of compounds identified as compounds exhibiting therapeutic properties in the treatment of IRS-2 related metabolic disorders or diseases, e.g. insulin regulating, e.g. insulin sensitizing or inhibiting properties, identified using the methods disclosed above.

Further, the present invention comprises a method, wherein the regulating elements regulating and/or contained in IRS-2 trancripts, in particular the sequences SEQ. ID. NO. 1 through 12, are used as drug targets to prevent or treat metabolic IRS-2 related disorders or diseases, e.g. diabetes and obesitas, in humans and/or animals.

According to one embodiment of the invention, an IRS-2 transcript is used for the manufacture of a medicament. In particular, a sequence chosen from SEQ. ID. NO. 1 through 12 or information derived therefrom is used for the manufacture of a medicament.

According to one embodiment of the invention, an IRS-2 transcript is used for the manufacture of a medicament for the treatment of diabetes. In particular, a sequence chosen from SEQ. ID. NO. 1 through 12 or information derived therefrom is used for the manufacture of a medicament for the treatment of metabolic, IRS-2 related disorders or diseases, e.g. diabetes or obesitas.

Further, the sequence information derived from an IRS-2 transcript and in particular the information contained in at least one of the sequences SEQ. ID. NO. 1–12, can be used for the manufacture of a medicament, in particular a medicament for the treatment of diabetes or obesitas.

Further, the sequence information derived from an IRS-2 transcript and in particular the information contained in at least one of the sequences SEQ. ID. NO. 1–12, can be used in an assay for diagnosing diabetes and/or differentiating between various types or stages of the disease.

Further, the present invention makes available a method for determining if a patient in need of treatment with an insulin regulating, e.g. insulin sensitizing substance has the predisposition to respond to the treatment, wherein the activation of IRS-2 is measured, e.g. by determining the amount or relative increase/decrease of the IRS-2 protein, or the corresponding mRNA when administering the insulin regulating substance in question to a sample of cells taken from the patient. The cells taken from the patient are chosen among blood cells, adipocyte cells, muscle cells or liver cells, preferably blood cells or adipocyte cells.

Further, the present invention makes available a method for determining if a patient in need of treatment with an insulin regulating, e.g. insulin sensitizing substance has the predisposition to respond to the treatment, wherein at least one sequence chosen among SEQ.ID.NO. 1–12 is used as a marker when administering the insulin regulating substance in question to a sample of cells taken from the patient. The cells taken from the patient are chosen among blood cells, adipocyte cells, muscle cells or liver cells, preferably blood cells or adipocyte cells.

The results also support the conclusion that thiazolidinediones, such as pioglitazone, have new specific modes of action and that they thus can be used as medicaments with specific therapeutic actions. The present invention thus comprises the use of thiazolidinediones, such as pioglitazone, for the manufacture of a medicament specifically for regulating the insulin sensitivity of particular cells, e.g. for increasing the insulin sensitivity of adipocytes.

EXAMPLE

1. Materials and Methods 1.1 Cell Cultures

3T3-L1 fibroblasts were grown and differentiated into adipocytes according to Rubin et al., 1977). At least 90% of the cells had acquired the adipocyte phenotype 6 days after initiating differentiation. Eight days after differentiation, the medium was changed and the various agents added for the times indicated in the Results.

To study the acute effect of insulin, the cells were serum-deprived for 3 hrs before adding 100 nM insulin for 15 min. Cell lysates were made using procedures previously described by Rondinone, et al 1997).

1.2 Analyses of RNA

Total cellular RNA was isolated from cells with guanidinium thiocyanate, as described (Chirgwin et al. 1979). Northern blot analyses were performed on total cellular RNA (30 μg) with labeled cDNA probes made against β-actin as housekeeping gene, mouse IRS-1 (bp 1333–2335) and mouse IRS-2 (bp 2987–3325) (kindly provided by Drs. J. Pierce and L-M Wang, NCI, NIH), rodent GLUT4 (bp 121–2128, Accession Nr NM 001042, kindly provided by Dr. Sam W. Cushman, NIDDK, NIH) and PKB/Akt using a PCR fragment against PKBβ (bp 282–1130, Accession Nr M95936) in a common sequence for PKBα, PKBβ and PKBγ. 5' sequence CGAGAGGCCGCGACCCAACAC and 3' sequence AGGCGGCCGCACATCATCTCGTA were used as PCR primers (SEQ. ID. NO. 13 and 14, respectively).

1.3 Immunoprecipitations and Immunoblotting

Cell lysates were prepared as described by Rondinone et al. 1997. Equal amounts of protein were separated by SDS/PAGE, transferred and immunoblotted with appropriate antibodies against the specific proteins. Phosphotyrosines were immunoblotted with antibody PY99 (Transduction Laboratories, Lexington, N.Y.), GLUT4 with an antibody kindly provided by Dr. Sam W. Cushman (NIDDK, NIH), IRS-1 and IRS-2 with antibodies from Upstate Biotechnology, Inc. (Lake Placid, N.Y.) and PKB/Akt with antibodies from Biolab (Boston, Mass.).

Immunoprecipitations were performed as described (Rondinone et at., 1997) and individual proteins were detected by blotting with horseradish peroxidase-linked secondary antibodies and using enhanced chemiluminescence (Nycomed Amersham plc., UK).

1.4 Sequencing of Human IRS-2 Transcripts

The 10 Kb genomic sequence immediately upstream of the open reading frame of the human IRS-2 gene was sequenced using ABI PRISM® BigDye™ Terminator Cycle Sequencing Ready Reaction Kit (Applied Biosystems) according to the manufacturers instructions.

2. Results

2.1 Effects of PPAR Agonists and/or Insulin on IRS-1/2, PXB and GLUT4 Gene and Protein Expression The expression of several genes involved in insulin signaling and action were examined after 4–48 hrs exposure to different concentrations of pioglitazone (pio). However, only the IRS-2 gene expression was consistently increased. The IRS-2 mRNA included a major ~7.2 Kb band but a minor band at ~8.2 Kb was also frequently seen. It is not clear at the time of filing the present application whether this represents alternative splicing of the same gene.

Figure 1B:
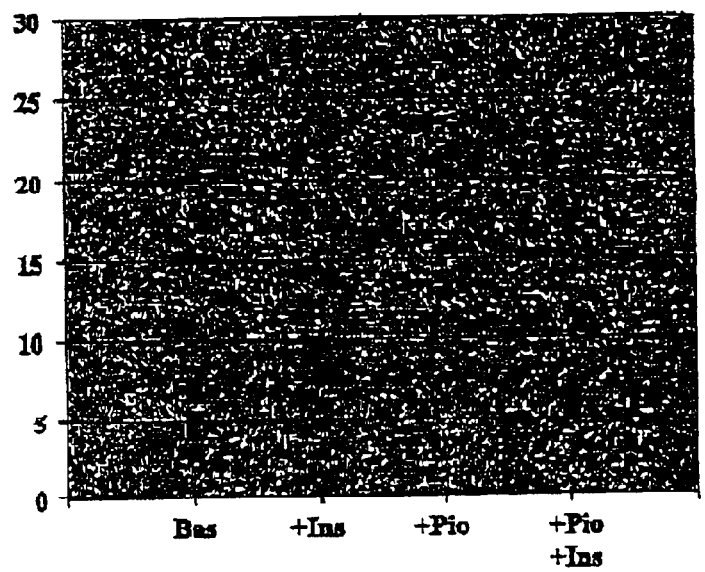
Figure 1B:
Figure 1B:
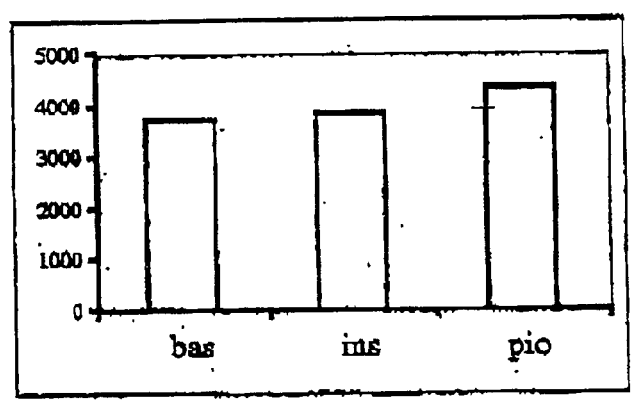

FIG. 1A (top) shows that insulin alone did not change IRS-2 gene expression while the addition of pioglitazone increased IRS-2 mRNA ~4-fold. This was due to an effect of pioglitazone alone and no further increase was seen by the addition of insulin (FIG. 1A—bottom). After 48 hrs, the IRS-2 mRNA levels were, consistently increased 3–5-fold relative to β-actin mRNA (FIG. 1B—top). IRS-2 protein expression was also increased by pioglitazone but not changed by insulin (FIG. 1B—bottom). The average increase seen after 48 hrs with pioglitazone was 36% (n=3).

Figure 1C:
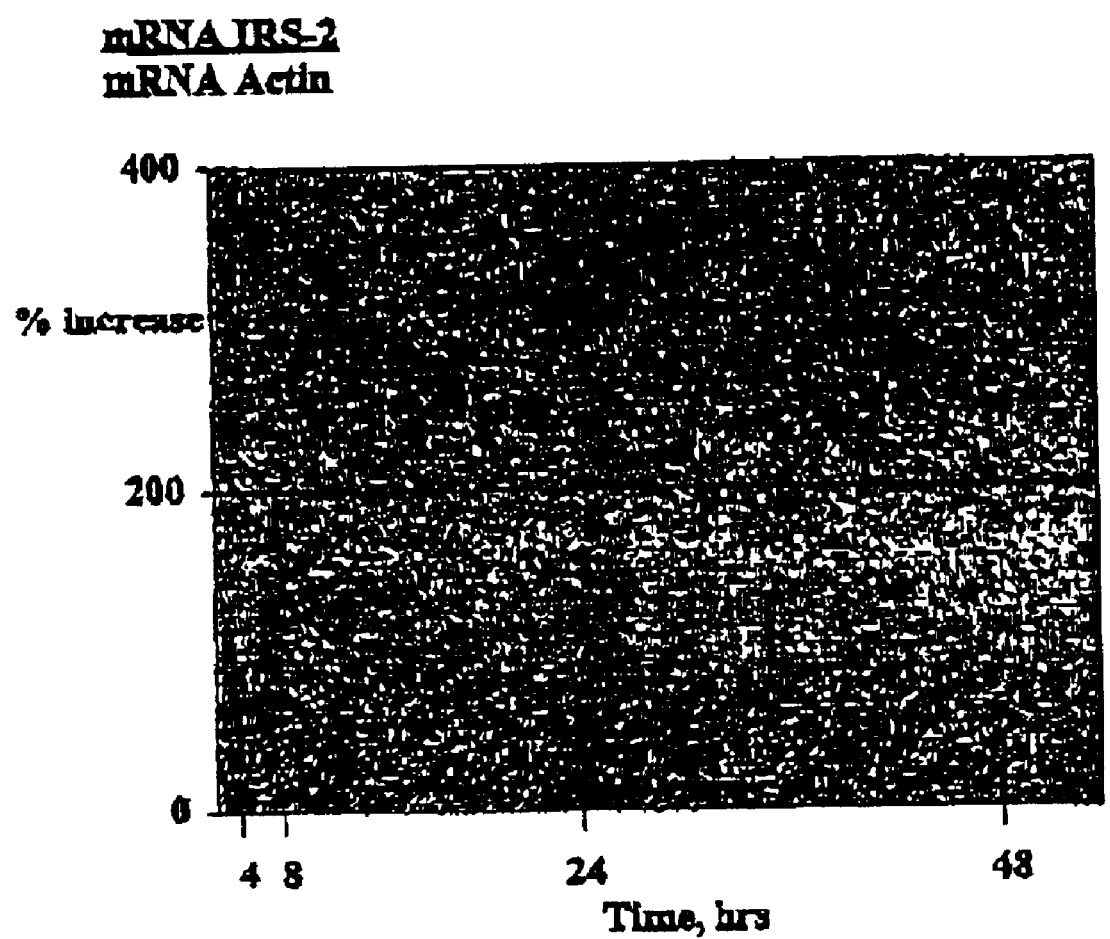

Time-course experiments showed that the gene expression was already increased after 4 hrs, peaked after 24 hrs but remained elevated throughout the 48 hrs observation time (FIG. 1C). This increase was specific for IRS-2 and remained irrespective of whether the IRS-2 expression was related to β-actin, IRS-1 or PKB mRNA levels (data not shown). The present inventor also examined if the rapid effect of pioglitazone was direct or required protein synthesis by adding cycloheximide (40 μM to the incubation medium for 8 and 24 hrs. However, pioglitazone also increased the IRS-2 mRNA expression in the presence of cycloheximide, suggesting a direct effect of pioglitazone on the IRS-2 gene (not shown).

The present inventor also examined whether a lower pioglitazone concentration increased IRS-2 mRNA expression. A similar effect was seen with 1 μM pioglitazone (average increase 230%, n=2) as with 10 μM in the same experiments (average increase 292%, n=2). Furthermore, darglitazone, another PPARγ ligand, induced a similar increase as pioglitazone (FIG. 2—top) while a specific PPARα ligand (WY14643) was completely without effect (average increase 9%, n=2) even at a high concentration (10 μM) and when insulin was added (FIG. 2—middle).

Thus, these data show that PPARγ, but not PPARα, ligands increase IRS-2 gene expression in 3T3-L1 adipocytes. The inventor also tested whether progesterone or 8-BrcAMP, which have been shown to increase IRS-2 gene expression in HeLa cells, also altered the expression in 3T3-L1 cells. However, no effects were seen even with high concentrations of these agents. However, when combined, the stimulating effect of pioglitazone was again shown (FIG. 2—bottom).

Neither insulin alone nor when combined with the PPARγ ligands, pioglitazone or darglitazone (not shown), altered the gene expression of IRS-1 or of PKB/Akt (FIG. 3A) in the same experiments. Similarly, no effect was seen with the PPARα agonist (data not shown). The PCR fragment used for PKB hybridization gave two major bands (3.2 and 2.8 Kb) probably reflecting both the PKBα/Akt 1 and the PKBβ/Akt 2 genes. Individual results of IRS-1 mRNA expression from five experiments are shown in FIG. 3B.

Similar to IRS-1, there was no consistent increase in GLUT4 mRNA expression by pioglitazone after 48 hrs incubation (data not shown).

Figure 3B:
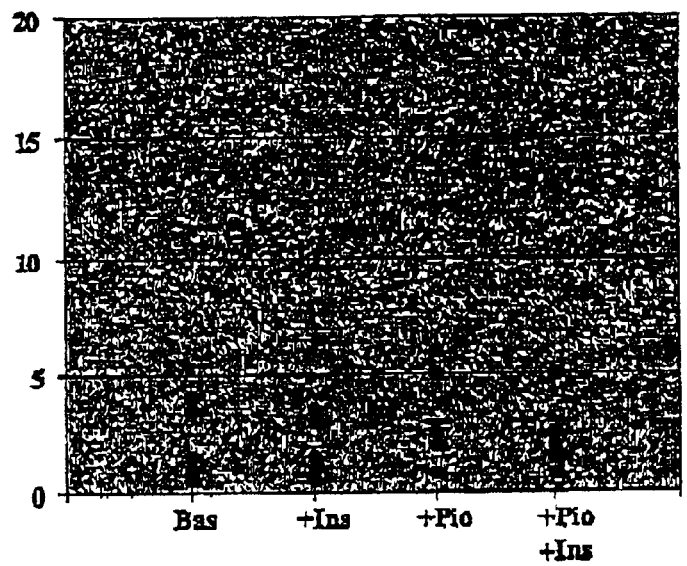
Figure 3B:
Figure 3B:
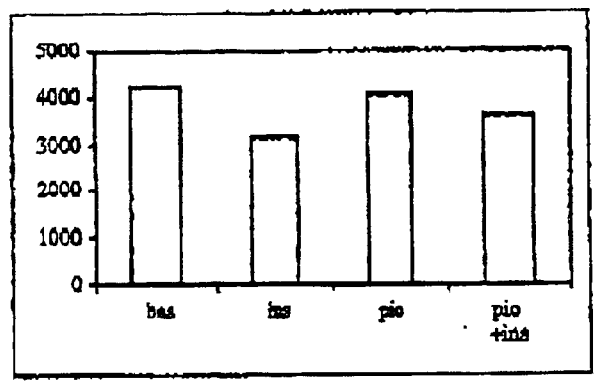

2.2 Effect of TZD and/or Insulin on IRS-1 Protein Expression and PKB/Akt Phosphorylation FIG. 3B (bottom) shows the chronic effects of pioglitazone and/or insulin on IRS-1 protein expression after 48 s. Pioglitazone alone did not change IRS-1 protein expression. However, in contrast to IRS-2 (FIG. 1B—bottom), IRS-1 protein expression was reduced by chronic stimulation with the high insulin concentration and this was not altered by the presence of pioglitazone (FIG. 3B—bottom).

In three experiments, insulin decreased IRS-1 protein expression by 33% (range 25–39%); this decrease remained unchanged when insulin and pioglitazone were combined (−31%, range 18–39%) while pioglitazone alone was without effect (+7%). These differences in protein expression were also reflected by the amount of p85 co-immuinoprecipitated with IRS-1 (not shown).

The present inventor also examined the acute effect of insulin on down-stream activation of PKB/Akt in cells that had been cultured with pioglitazone for 48 hrs, washed and serum-starved for 3 hrs in fresh medium. Similar to the gene (FIG. 3A), PKB/Akt protein expression was not changed by the presence of either pioglitazone and/or insulin for 48 hrs (not shown). Insulin (100 nM) was then added for 10 min to the serum-starved cells. As shown in FIG. 4, the acute effect of insulin on PKB/Akt phosphorylation tended to be increased in cells cultured with pioglitazone alone.

In contrast, chronic exposure to insulin alone markedly reduced the acute effect of insulin on PKB/Akt phosphorylation. The addition of pioglitazone for 48 hrs did not improve the reduced insulin-stimulated phosphorylation of PKB/Akt induced by the chronic hyperinsulinemia but an improvement was seen after 96 hrs.

The inventor has performed experiments with human adipocytes, which indicate that the results obtained with the 3T3-L1 adipocytes are transferable to human cells. The present inventor has shown that TZD increase IRS-2 expression in human adipocrytes after 24 hrs in culture. Thus, the results available at the priority date support a broad application of the invention.

During the priority year, 12 novel sequences were isolated and sequenced. The alignment chart shown in FIG. 5 shows that all these share the AGGTCA binding site for PPAR.

Although the invention has been described with regard to its preferred embodiments, which constitute the best mode presently known to the inventor, it should be understood that various changes and modifications as would be obvious to one having the ordinary skill in this art may be made without departing from the scope of the invention as set forth in the claims appended hereto.

References

Chirgwin, J. M., Przybyla, A. E., MacDonald, R. J. and Rutter, W. J. (1979) Isolation of biologically active ribonucleic acid from sources enriched in ribonuclease. *Biochemistry* 18, 5294–5299.

Mangelsdorf, D. J. and Evans, R. M. (1995) The RXR Heterodimers and Orphan Receptors *Cell* 83, 841–850.

Rondinone, C. M., Wang, L. M., Lonnroth, P., Wesslau, C., Pierce, J. H. and Smith, U. (1997) Insulin receptor substrate (IRS) 1 is reduced and IRS-2 is the main docking protein for phosphatidylinositol 3-kinase in adipocytes from subjects with non-insulin-dependent diabetes mellitus. *Proc Nalt Acad Sci USA* 94, 4171–4175.

Rubin, C. S., Lai, E. and Rosen, O. M. (1977) Acquisition of increased hormone sensitivity during in vitro adipocyte development. *J. Biol Chem* 252, 3554–3557.

Spiegelnan, B. M. (1998) PPARγ: adipogenic regulator and thiazolidinedione receptor. *Diabetes* 47, 507–514.

Sun, X. J., Pons, S., Wang, L. M., Zhang, Y., Yenash, L., Burks, D., Myers, M. G., Jr., Glasheen, E., Copeland, N. G., Jenkins, N. A., Pierce, J. H. and White, M. F. (1997) The IRS-2 gene on murine chromosome 8 encodes a unique signaling adapter for insulin and cytokine action. *Mol Endocrinol* 11, 251–262.

Vassen, L., Wegrzyn, W. and Klein-Hitpass, L. (1999) Human insulin receptor substrate-2: gene organization and promoter characterization. *Diabetes* 48, 1877–1880.

What is claimed is:

1. An isolated, substantially purified nuoleotide sequence, consisting of SEQ ID NO: 3 and wherein said nucleotide sequence is in a screening system and is a marker for compounds exhibiting insulin regulating properties.

2. The nucleotide sequence according to claim 1, wherein said sequence is a marker for thiazlidinedione (TZD) compounds.

3. The nucleotide sequence according to claim 1, wherein said sequence is a marker for adipocyte specific insulin regulating substances.

4. An isolated, substantially purified nucleotide sequence, consisting of SEQ ID NO:3 and wherein said nucleotide sequence is coupled to a reporter system and is a marker for compounds exhibiting insulin regulating properties.

5. The nucleotide sequence according to claim 4, wherein the reported system is a fluorescent reporter molecule.

6. The nucleotide sequence according to claim 4, wherein said sequence is a marker for thiazlidinedione (TZD) compounds.

7. The nucleotide sequence according to claim 4, wherein said sequence is a marker for adipocyte specific insulin regulating substances.

* * * * *